United States Patent [19]

Gorman et al.

[11] Patent Number: 5,378,451
[45] Date of Patent: Jan. 3, 1995

[54] TOPICAL MEDICINAL PRESSURIZED AEROSOL COMPOSITIONS AND METHOD OF PREPARATION, METHOD OF USE AND ARTICLE OF MANUFACTURE THEREOF

[75] Inventors: William G. Gorman, East Greenbush; Fred A. Carroll, III, Sand Lake, both of N.Y.

[73] Assignee: Dow B. Hickam, Inc., Sugarland, Tex.

[21] Appl. No.: 126,747

[22] Filed: Sep. 27, 1993

Related U.S. Application Data

[63] Continuation of Ser. No. 424,047, Oct. 19, 1989, abandoned.

[51] Int. Cl.$^6$ ............................................. A61K 7/00
[52] U.S. Cl. .................................... 424/47; 424/44; 424/45
[58] Field of Search ................... 424/47, 45, 445, 448, 424/619

[56] References Cited

U.S. PATENT DOCUMENTS

| | | | |
|---|---|---|---|
| 3,969,498 | 7/1976 | Catania et al. | 424/45 |
| 4,065,472 | 12/1977 | Schaaf et al. | 514/841 |
| 4,391,799 | 7/1983 | Mason, Jr. et al. | 514/779 |
| 4,393,048 | 7/1983 | Mason, Jr. et al. | 514/944 |
| 4,534,958 | 8/1985 | Adams et al. | 424/45 |

FOREIGN PATENT DOCUMENTS 1372721 11/1974 United Kingdom .

OTHER PUBLICATIONS

The Merck Index, Tenth Edition, 1983, title page and monograph 5466.

*Primary Examiner*—Thurman K. Page
*Assistant Examiner*—William E. Benston, Jr.
*Attorney, Agent, or Firm*—Vinson & Elkins

[57] ABSTRACT

Topical medicinal pressurized aerosol compositions and method of preparation, method of use and article of manufacture thereof especially wherein the topical medicament is mafenide or a pharmaceutically acceptable acid addition salt thereof, most especially mafenide acetate, and especially for treatment of burns are disclosed.

26 Claims, No Drawings

TOPICAL MEDICINAL PRESSURIZED AEROSOL COMPOSITIONS AND METHOD OF PREPARATION, METHOD OF USE AND ARTICLE OF MANUFACTURE THEREOF

This is a continuation of copending application Ser. No. 07/424,047, filed Oct. 19, 1989, now abandoned.

FIELD OF THE INVENTION

The invention relates to topical medicinal pressurized aerosol compositions and method of preparation, method of use and article of manufacture thereof, especially wherein the topical medicament is mafenide or a pharmaceutically acceptable acid addition salt thereof, most especially mafenide acetate, and especially for treatment of burns.

INFORMATION DISCLOSURE STATEMENT

Mafenide and the hydrochloride, acetate and propionate salts thereof are described by monograph 5466 of The Merck Index (Tenth Edition, 1983).

British Pat. 1,372,721 (Wilkinson Sword Limited; Ronald James, inventor) published Nov. 6, 1974 describes a container of antiseptic for the treatment of burns and scalds by topical application, containing a topically acceptable antiseptic active agent [sic, against] *Pseudomonas aeruginosa*, a pressurising agent and at least one surfactant admixed with water, said container comprising an outlet, and valve means operable to allow discharge of the contents of the container through said outlet in the form of a foam which is effective in the control of *Pseudomonas aeruginosa* at the site of a burn or scald.

A specifically described topically acceptable antiseptic is a salt of "α-amino-p-toluene-sulphonamide" (mafenide), preferably "a water soluble salt such as an acetate, hydrochloride, lactate, or tartrate". One example (Example 12) is described wherein the topically acceptable antiseptic is α-amino-p-toluene-sulphonamide acetate (mafenide acetate).

Adams et al. (BASF Wyandotte Corporation) U.S. Pat. No. 4,534,958 issued Aug. 13, 1985 describes and claims "a sprayable aerosol foam treatment composition which is a liquid in the aerosol container and forms a gel upon application to the skin" comprising water, propellant, volatile solvent, and a polyoxyethylene-polyoxypropylene copolymer whose function is not described and optionally also including a burn treatment agent and one or more adjuvants and method of use thereof "for treating living skin". Mafenide acetate is not specifically named as a burn treatment agent. Each of the compositions of the five examples is described as becoming "a foamy gel as the solvent and propellant evaporated providing protection for the burn".

A need exists, especially in the burn treatment field, for a topical medicinal pressurized aerosol composition which is dischargeable from an aerosol dispenser as a spray that forms a stable foam on the application site. The presently described and claimed invention fills this need. Neither British Pat. 1,372,721 nor Adams et al. U.S. Pat. No. 4,534,958 describes such a composition. The compositions of British Pat. 1,372,721 including that of Example 12, which has been made and tested as described below, are discharged not as sprays but as foams and those of Adams et al. U.S. Pat. No. 4,534,958 form gels on the application site.

SUMMARY OF THE INVENTION

In a composition of matter aspect the invention is a topical medicinal pressurized aerosol composition consisting essentially of by weight/weight from about 0.1% to about 15% of a topical medicament or a mixture of two or more topical medicaments, from about 3% to about 20% of a liquified propellant or a mixture of two or more liquified propellants, from about 20% to about 80% of an aqueous vehicle, and from about 0.1% to about 10% of a nonionic polyoxyethylene surfactant or a mixture of two or more nonionic polyoxyethylene surfactants each having at least 80% by molecular weight of oxyethylene units, said composition being dischargeable from an aerosol dispenser as a spray that forms a stable foam on the application site.

In a first process aspect the invention is the method of preparing an above-described composition which comprises mixing the ingredients thereof without the liquified propellant and then charging the resulting mixture together with the liquified propellant into and aerosol dispenser.

In a second process aspect the invention is the method of using an above-described composition which comprises discharging said composition from an aerosol dispenser as a spray that forms a stable foam on the application site.

In a manufacture aspect the invention is an above-described composition contained within an aerosol dispenser which discharges said composition as a spray that forms a stable foam on the application site.

DETAILED DESCRIPTION OF THE INVENTION INCLUSIVE OF THE PREFERRED EMBODIMENTS

The topical medicament can be any medicinal compound which is stable on admixture with the other ingredients of the pressurized aerosol composition and effective on topical administration or a combination of any two or more such compounds and is preferably selected from the group consisting of antimicrobials, antivirals, antiinflammatories, anesthetics and astringents. The antimicrobial is preferably selected from the group consisting of mafenide and the pharmaceutically acceptable acid addition salts thereof, especially mafenide acetate, silver sulfadiazine, chlorhexidine and the pharmaceutically acceptable acid addition salts thereof, povidone-iodine, benzalkonium chloride, methylbenzethonium chloride, benzethonium chloride, cetylpyridinium chloride, 8-hydroxyquinoline, chlorothymol, chlorbutanol, triclosan, bacitracin, neomycin, polymixin, gentamicin, tetracyline, mupirocin, tolnaftate and miconazole. The preferred antiviral is acyclovir. The preferred antiinflammatory is selected from the corticosteroids, preferably hydrocortisone and esters thereof and fluocinolone acetonide. The preferred anesthetic is selected from the group consisting of benzocaine, lidocaine, tetracaine, butamben, diperodon, dibucaine, dibucaine hydrochloride, benzyl alcohol, dimethisoquin hydrochloride, phenol and dyclonine hydrochloride. The preferred astringent is hamamelis (witch hazel).

The liquified propellant can be any pharmaceutically acceptable liquified propellant having a vaper pressure alone or in mixture from about 20 p.s.i.g. to about 130 p.s.i.g. and is preferably selected from the group consisting of propane, butane, isobutane, dichlorodifluoromethane, monochlorodifluoromethane, dichlorotrifluoroethane, monochlorotetrafluoroethane, tetrafluoroethane, dichloromonofluoroethane and difluoroethane.

The aqueous vehicle is mostly (about 80% or more by weight/weight) water but may contain by weight/weight from about 1% to about 20% of humectant or a mixture of two or more humectants selected from the group consisting of the polyhydric alcohols and polyvinylpyrrolidone. The polyhydric alcohols are preferably selected from the group consisting of propylene glycol, butylene glycol, the polyethylene glycols, glycerol and sorbitol.

The nonionic polyoxyethylene surfactant having at least 50% by molecular weight of oxyethylene units is selected from the group consisting of the polyethylene glycol ethers of alkanols having 12–22 carbon atoms, alkylphenols and dialkylphenols having 14–24 carbon atoms, lanolin alcohol, sterols and alkanoate esters of propylene glycol, glycerol and sorbitol having 12–18 carbon atoms in alkanoate; the polyethylene glycol esters of alkanoic acids having 8–18 carbon atoms; and the polyethylene glycol derivatives of castor oil, hydrogenated castor oil, lanolin and hydrogenated lanolin. All of these classes of nonionic polyoxyethylene surfactants are known and examples of all of them are commercially available and are listed and defined by the CTFA Cosmetic Ingredient Dictionary (Third Edition, 1982; The Cosmetic, Toiletry and Fragrance Association, Inc. 1110 Vermont Avenue, N.W. Wash., 20005) and supplements thereof. Table I shows at least one example of each class and the definition thereof.

pyl myristate and isopropyl palmitate. The lipophilic surfactants include, for example, glyceryl stearate, glyceryl oleate, glyceryl myristate, glyceryl laurate sorbitan trioleate, sorbitan tristearate, sorbitan trilaurate sorbitan monostearate, sorbitan monooleate, steareth-1, steareth-2, ceteth-1, ceteth-2, laureth-1, laureth-2, oleth-1 and oleth-2.

Since the compositions of the invention are intended for human or animal application, they also desirably contain from about 0.1% to about 1% of a preservative against microbial contamination, which is preferably selected from the group consisting of methylparaben, ethylparaben, propylparaben, butylparaben, imidurea, quaternium 15, sorbic acid, 2-bromo-2-nitropropane-1,3-diol, dehydroacetic acid, benzoic acid, benzalkonium chloride, benzethonium chloride, phenoxyethanol, benzyl alcohol, cetylpridinium chloride and chlorobutanol.

A pharmaceutically acceptable acid or base or buffer for adjustment or maintenance of pH may also be added.

The compositions are generally prepared by mixing the ingredients without the liquified propellant at a temperature in the range of 0°–100° C. and ambient pressure and then charging the resulting mixture together with the liquified propellant into an aerosol dispenser to achieve the final composition. Mixing is preferably carried out at a temperature in the range of 20°–80° C.

The aerosol dispenser can be a conventional aerosol can or bottle having a conventional continous spray aerosol valve. A desirable feature of the dispenser, espe-

TABLE I

| CTFA Adopted Name | Nonionic Polyoxyethylene Surfactants CTFA Cosmetic Ingredient Dictionary Definition |
|---|---|
| Ceteth - 45 | the polyethylene glycol ether of Cetyl Alcohol that conforms to the formula $CH_3(CH_2)_{14}CH_2-(OCH_2CH_2)_nOH$ where n has an average value of 45 |
| Nonoxynol - 40 | the ethoxylated alkyl phenol that conforms generally to the formula $C_9H_{19}C_6H_4(OCH_2CH_2)_nOH$ where n has an average value of 40 |
| Laneth - 75 | the polyethylene glycol ether of Lanolin Alcohol with an average ethoxylation value of 75 |
| PEG - 40 Soya Sterol | a polyethylene glycol derivative of sterols found in Soybean Oil with an average of 40 moles of ethylene oxide |
| PEG-120 Glyceryl Stearate | the polyethylene glycol ether of Glyceryl Stearate that conforms generally to the formula $CH_3(CH_2)_{16}COOCH_2-CH(OH)CH_2(OCH_2CH_2)_nOH$ where n has an average value of 120 |
| PEG - 40 Stearate | the polyethylene glycol ester of stearic acid that conforms to the formula $CH_3(CH_2)_{16}CO(OCH_2CH_2)_nOH$ where n has an average value of 40 |
| PEG - 100 Stearate | the polyethylene glycol ester of stearic acid that conforms to the formula $CH_3(CH_2)_{16}CO(OCH_2CH_2)_nOH$ where n has an average value of 100 |
| PEG -60 Castor Oil | a polyethylene glycol derivative of Castor Oil with an average of 60 moles of ethylene oxide |
| PEG - 75 Lanolin | a polyethylene glycol derivative of Lanolin with an average of 75 moles of ethylene oxide |

The compositions of the invention are essentially oil-in-water type emulsions, which if desired can be modified by addition of from about 1% to about 5% of one or more lipophilic compounds or lipophilic surfactants. The lipophilic compounds include the fatty alcohols, fatty acids and oils. The fatty alcohols include, for example, lauryl alcohol, myristyl alcohol, cetyl alcohol, stearyl alcohol and oleyl alcohol. The fatty acids include, for example, lauric acid, myristic acid, palmitic acid, stearic acid, isostearic acid and oleic acid. The oils include, for example, mineral oil, petrolatum, cottonseed oil, coconut oil, sesame seed oil, peanut oil, isoprocially for burn treatment compositions, is an all position valve that permits spraying when the dispenser is held at any angle so that horizontal bottom surfaces as well as horizontal top surfaces and vertical surfaces can be sprayed. The valve actuator must be one which produces a spray and not a foam at the nozzle. A preferred valve actuator is a mechanical breakup actuator, which employs mechanical forces rather than expansion and evaporation of the propellant to produce a spray. A typical mechanical breakup actuator has a conical or cylindrical swirl chamber with an inlet channel oriented perpendicular to the axis thereof. This structure imparts a swirling motion to the aerosol mixture upon discharge. The swirling motion occurs around the axis of the swirl chamber forming a thin conical film of discharged mixture, which breaks into droplets as it leaves the swirl chamber and travels in the direction of the axis thereof. The result is a fine, soft, dispersed spray which can be easily controlled to produce a stable, nonrunny foam of even thickness completely contacting the application site. In dispensing a composition of the invention the aerosol dispenser can typically be held about 6 to 12 inches (15-30 cm.) from the application site and produces a foam about a quarter of an inch (6 mm.) in thickness thereon. An aerosol dispenser which produces a foam at the nozzle must be held much closer to the application site becaure the foam can only be removed from the nozzle and applied to the application site by contacting the foam with the application site, and thus produces thick and uneven applications of foam.

The following composition of the invention was prepared by mixing the ingredients except the liquified propellant with heating up to about 70° C. and then cooling to about 25° C. and then charging the mixture together with the liquified propellant into a conventional aerosol can having a conventional continuous spray aerosol valve permitting spraying at any angle and a mechanical breakup actuator.

| Ingredient | Percent by Weight/Weight |
|---|---|
| Mafenide Acetate | 5.00 |
| Glycerin | 8.00 |
| Myristyl Alcohol | 2.00 |
| PEG-40 Stearate | 4.00 |
| Glyceryl Stearate and PEG-100 Stearate[a] | 2.00 |
| Methylparaben | 0.300 |
| Purified Water | 71.7 |
| Propane - isobutane (16:84)[b] | 7.00 |
| | 100.0 |

[a]Arlacel 165 (ICI Americas)
[b]Hydrocarbon 46, vapor presure 46 psig. at 70° F.

This composition was discharged from the aerosol dispenser as a fine, soft, dispersed spray which could easily be controlled to produce a stable, nunrunny, completely contacting foam of even thickness on a target surface, for example, a laboratory cover glass. This foam was observed to last for at least 24 hours.

The result with this composition is considered to be a significant advance in the art of medicinal pressurized aerosol compositions, especially for burn treatment because it permits application of a burn treatment medicament (mafenide acetate) by a method whereby the wound of the burn victim need not be touched except by the foam-forming spray itself. The method is equally adaptable to emergency conditions at the time and place of the burn occurrence as well as to emergency room or hospital room conditions. The foam is easily washable from the application site by water in preparation for examination of the wound and reapplication of the foam or other treatment.

For purpose of comparison Example 12 of above-cited British Pat. 1,372,721 was prepared and charged into the same kind of aerosol can having the same kind of aerosol valve and the same kind of mechanical breakup actuator as those of the foregoing example. The composition was not dischargeable as a spray but instead formed a foam at the nozzle. Upon contacting the foam with a laboratory cover glass in order to remove it from the nozzle and coat the cover glass, only a coating of much greater thickness than possible with the foregoing example and of uneven thickness and incomplete contact with the cover glass as seen from the underside thereof was formed.

We claim:

1. A topical medicinal pressurized aerosol composition consisting essentially of by weight/weight from about 0.1% to about 15% of a topical medicament or a mixture of two or more topical medicaments, wherein the topical medicament is selected from the group consisting of antimicrobials, antivirals, antiinflammatories, anesthetics and astringents, from about 3% to about 20% of a liquified propellent or a mixture of two or more liquified propellants, wherein the liquid propellant has a vapor pressure alone or in mixture from about 20 p.s.i.g. to about 130 p.s.i.g., from about 20% to about 80% of an aqueous vehicle, wherein the aqueous vehicle contains from about 1% to about 20% of a humectant or a mixture of two or more humectants selected from the group consisting of the polyhydric alcohols and polyvinylpyrrolidone, and from about 0.1% to about 10% of a nonionic polyoxyethylene surfactant or a mixture of two or more nonionic polyoxyethylene surfactants each having at least 80% by molecular weight of oxyethylene units, said composition being dischargeable from an aerosol dispenser as a spray that forms a stable foam on the application site.

2. A composition according to claim 1 wherein the topical medicament is an antimicrobial.

3. A composition according to claim 1 wherein the topical medicament is mafenide or a pharmaceutically acceptable acid addition salt thereof.

4. A composition according to claim 2 wherein the topical medicament is mafenide acetate.

5. A composition according to claim 3 wherein the liquid propellant is selected from a group consisting of propane, butane, isobutane, difluoromethane, monochlorodiflouromethane, dichlorotriflouromethane, monochlorotetrafluoroethane, tetraflouroethane, dichloromonoflouroethane, and difluoroethane or a mixture of two or more thereof.

6. A composition according to claim 5 wherein the liquified propellant is a propane-isobutane (16:84)mixture and has a vapor pressure of 46 p.s.i.g. at 70° F.

7. A composition according to claim 5, wherein the humectant is glycerol.

8. A composition according to claim 6 wherein the nonionic polyoxyethylene surfactant having at least 80% by molecular weight of oxyethylene units is selected from the group consisting of the polyethylene glycol ethers of alkanols having 12–22 carbon atoms, alkylphenols and dialkylphenols having 14–24 carbon atoms, lanolin alcohol, sterols and alkanoate esters of propylene glycol, glycerol and sorbitol having 12–18 carbon atoms in alkanoate; the polyethylene glycol esters of alkanoic acids having 8–18 carbon atoms; and the polyethylene glycol derivatives of castor oil, hydrogenated castor oil, lanolin and hydrogenated lanolin.

9. A composition according to claim 1 wherein the nonionic polyoxyethylene surfactant having at least 80% by molecular weight of polyoxyethylene units is a polyethylene glycol ester of an alkanoic acid having 8–18 carbon atoms or a mixture of two or more thereof.

10. A composition according to claim 9 wherein the polyethylene glycol ester of an alkanoic acid having 8-18 carbon atoms or a mixture of two or more thereof is a mixture of the polyethylene glycol ester of stearic acid that conforms to the formula $CH_3(CH_2)_{16}CO(OCH_2CH_2)_nOH$ where n has an average value of 40 and the polyethylene glycol ester of stearic acid that conforms to the formula $CH_3(CH_2)_{16}CO(OCH_2CH_2)_pOH$ where p has an average value of 100.

11. The method of preparing a composition according to claim 1 which comprises mixing the ingredients thereof without the liquified propellant and then charging the resulting mixture together with the liquified propellant into an aerosol dispenser.

12. The method according the claim 9 wherein the mixing is carried out at a temperature in the range of 0°–100° C.

13. The method according to claim 10 wherein the mixing is carried out at a temperature in the range of 20°–80° C.

14. The method of using a composition according to claim 1 which comprises discharging said composition from an aerosol dispenser as a spray that forms a stable foam on the application site.

15. A composition according to claim 1 contained within an aerosol dispenser which discharges said composition as a spray that forms a stable foam on the application site.

16. A composition according to claim 13 wherein the aerosol dispenser has a mechanical breakup actuator.

17. A topical medicinal pressurized composition consisting of by weight/weight from about 1% to about 10% mafenide acetate, from about 1% to about 10% glycerin, from about 1% to about 5% myristyl alcohol, from about 1% to about 10% of the polyethylene glycol ester of stearic acid that conforms to the formula $CH_3(CH_2)_{16}CO(OCH_2CH_2)_nOH$ where n has an average value of 40, from about 1% to about 10% of a mixture of glyceryl stearate and the polyethylene glycol ester of stearic acid that conforms to the formula $CH_3(CH_2)_{16}CO(OCH_2CH_2)_pOH$ where p has an average value of 100, from about 0.1% to about 1% of a preservative, from about 60% to about 80% purified water and from about 3% to about 10% of a propane-isobutane mixture, said composition being dischargeable from an aerosol dispenser having a mechanical breakup actuator as a spray that forms a stable foam on the application site.

18. A composition according to claim 15 consisting of by weight/weight 5% mafenide acetate, 8% glycerin, 2% myristyl alcohol, 4% of the polyethylene glycol ester of stearic acid that conforms to the formula $CH_3(CH_2)_{16}CO(OCH_2CH_2)_nOH$ where n has an average value of 40, 2% of a mixture of glyceryl stearate and the polyethylene glycol ester of stearic acid that conforms to the formula $CH_3(CH_2)_{16}CO(OCH_2CH_2)_pOH$ where p has an average value of 100, 0.3% methylparaben, 71.7% purified water and 7% propane-isobutane(16:84).

19. The method of preparing a composition according to claim 15 which comprises mixing the ingredients thereof without the propane-isobutane and then charging the resulting mixture together with the propane-isobutane into an aerosol dispenser.

20. The method of preparing a composition according to claim 16 which comprises mixing the ingredients thereof without the propane-isobutane and then charging the resulting mixture together with the propane-isobutane into an aerosol dispenser.

21. The method of using a composition according to claim 15 which comprises discharging said composition from an aerosol dispenser as a spray that forms a stable foam on the application site.

22. The method of using a composition according to claim 16 which comprises discharging said composition from an aerosol dispenser as a spray that forms a stable foam on the application site.

23. The method according to claim 20 wherein the application site is a burn wound.

24. A composition according to claim 15 contained within an aerosol dispenser which discharges said composition as a spray that forms a stable foam on the application site.

25. A composition according to claim 18 contained within an aerosol dispenser which discharges said composition as a spray that forms a stable foam on the application site.

26. A composition according to claim 25 wherein the aerosol dispenser has a mechanical breakup actuator.

* * * * *